United States Patent [19]  
Masuho et al.

[11] Patent Number: 4,950,595  
[45] Date of Patent: Aug. 21, 1990

[54] MOUSE-HUMAN HYBRIDOMA WHICH PRODUCES ANTIVIRUS-HUMAN ANTIBODY, PROCESS FOR PREPARATION THEREOF, AND ANTIVIRUS-HUMAN MONOCLONAL ANTIBODY

[75] Inventors: Yasuhiko Masuho, Hino; Yoh-ichi Matsumoto, Tokyo; Toru Sugano, Machida; Katsuhiko Tomibe, Tokyo, all of Japan

[73] Assignee: Teijin Limited, Osaka, Japan

[21] Appl. No.: 871,436

[22] PCT Filed: Sep. 27, 1985

[86] PCT No.: PCT/JP85/00537
§ 371 Date: May 28, 1986
§ 102(e) Date: May 28, 1986

[87] PCT Pub. No.: WO86/02092
PCT Pub. Date: Apr. 10, 1986

[30] Foreign Application Priority Data

Sep. 28, 1984 [JP] Japan .................................. 59-201992  
Oct. 8, 1984 [JP] Japan .................................. 59-209630  
Apr. 10, 1985 [JP] Japan .................................. 60-74520

[51] Int. Cl.$^5$ .................... C12P 21/00; C12N 5/00; C21N 33/53
[52] U.S. Cl. ................. 530/387; 435/240.21; 435/240.26; 435/240.27; 435/172.2; 435/70.21; 436/548; 935/95; 935/99; 935/100; 935/103; 935/104

[58] Field of Search .............. 435/240.26, 240.27, 435/240.21, 68, 172.2; 530/387; 436/548; 935/95, 99, 100, 103, 104

[56] References Cited

U.S. PATENT DOCUMENTS 4,574,116 3/1986 Kaplan ................................... 435/68  
4,634,666 1/1987 Engleman et al. .................... 435/68

FOREIGN PATENT DOCUMENTS 2113715A 6/1983 United Kingdom .

OTHER PUBLICATIONS

Campbell Laboratory Techniques in Biochem. & Mol. Biology, vol. 13, Elsevier, Amsterdam, 1984, pp. 94–99.  
Okuno, T. et al. Virology 129, pp. 357–368, 1983.  
Nowinski et al., Science, 120, pp. 537–539, 1980.  
Foung, S. et al., J. Inf. Diseases 152, pp. 280–285, 1985.

Primary Examiner—Christine M. Nucker  
Assistant Examiner—Karen I. Krupen  
Attorney, Agent, or Firm—Sughrue, Mion, Zinn, Macpeak & Seas

[57] ABSTRACT

Mouse-human hybridoma, which produces monoclonal antivirus-human antibody reactive to herpes simplex virus, varicella zoster virus, and cytomegalo virus, obtained by allowing a human antibody cell, which is sensitized to virus or protein or glycoprotein arising from virus, to fuse with a mouse myeloma cell in the presence of mitogen in vitro.

11 Claims, 2 Drawing Sheets

MOUSE-HUMAN HYBRIDOMA WHICH PRODUCES ANTIVIRUS-HUMAN ANTIBODY, PROCESS FOR PREPARATION THEREOF, AND ANTIVIRUS-HUMAN MONOCLONAL ANTIBODY

TECHNICAL FIELD

The present invention relates to a mouse-human hybridoma which produces an antivirus-human antibody, a process for the preparation thereof, and an antivirushuman monoclonal antibody.

It is an object of this invention to provide a mouse-human hybridoma which produces an antivirus-human antibody that is useful for making a diagnosis and providing a cure for viral diseases caused by herpes simplex virus (HSV), varicella zoster virus (VZV), cytomegalo virus (CMV), influenza virus, rabies fixed virus, Japanese encephalitis virus, myxovirus (causing epidemic parotitis), hepatitis B virus (HBV), rotavirus, etc.

It is another object of this invention to provide an anti HSV human monoclonal antibody which is useful for making a diagnosis and providing a cure for viral diseases caused by HSV type 1 or 2. It is another object of the present invention to provide a human monoclonal antibody which reacts specifically to VZV and is useful for making a diagnosis and providing a cure for viral diseases caused by VZV.

BACKGROUND ART

It is a publicly known method to establish hybridoma (fused cell) which continuously produces and secrets a specific antibody by fusing a lymph corpuscle, or a B cell (an antibody-producing cell), which produces a specific antibody but is destined to perish in due course of time, with a myeloma cell, which continues to proliferate indefinitely in a culture medium, by utilizing the art of cell fusion. A monoclonal antibody produced by the hybridoma obtained according to such an art can be used as a pure chemical reagent of high accuracy and reliability and offers applications as a testing reagent, labelling reagent, and also in affinity chromatography. It is further expected to be used as drugs to cure and prevent various diseases.

It is accepted as general knowledge that an attempt to obtain a monoclonal virus antibody can be achieved by using a virus antibody-producing cell with a myeloma cell to give hybridoma, which is producible of a virus antibody, by cloning. Its concrete example is shown in Japanese patent application No. 2276/84, which discloses a process wherein a BALB/C mouse spleen cell, which is immunized to influenza virus or virus of rabies, is fused with a myeloma cell of a mouse of the same species to obtain a hybridoma, which is then subjected to cloning to give a hybridoma which produces a monoclonal antivirus-mouse antibody. Japanese patent application Laid-open No. 175489/83 also discloses that hybridoma which produces antiherpes simplex virus-mouse antibody was obtained by fusing a spleen cell of a mouse immunized to herpes simplex virus with a mouse myeloma cell.

As described in the above, definitely successful cases of antivirus antibody-producing hybridomas are limited only to the mouse-mouse hybridomas which produce antivirus-mouse antibodies. However, in case of making a diagnosis and providing a cure for human being disease, the use of an antivirus-human antibody comprising the homogeneous proteins is absolutely useful and safe, and this can be realized only by the established formation of a mouse-human hybridoma or a human-human hybridoma obtained by use of anti-body-producing cells of a human being. In the case of a human being, however, being different from the case of animals, there are problems which face us with difficulty of obtaining proper antibody-producing cells since it can not be arranged with ease to have a human being immunized to a large amount of viruses to get effectively stimulated antibody-producing cells for the desired cell fusion use, and there have been no reports made yet on definitely successful practices.

DISCLOSURE OF INVENTION

As the result of intensive research work made on obtaining mouse-human hybridomas producible of antivirus-human antibody, the present inventors have made it possible to obtain antivirus-human antibody-producing mouse-human hybridoma by the method of allowing a human antibody-producing cell sensitized with virus or protein, or glycoprotein arising from virus, to fuse with a mouse myeloma cell in the presence of mitogen in vitro. It has accordingly been actualized to obtain a human monoclonal antibody, which specifically reacts to HSV or VZV, from the culture in which a specially chosen hybridoma and/or a cell line arising therefrom has been cultivated.

BEST MODE FOR CARRYING OUT THE INVENTION

What is referred to as a human antibody-producing cell in the present invention is a human lymph cell (or B cell) which is a cell that secrets or is capable of secreting an antibody. Such a cell is found among the cells of the spleen, lymph node, peripheral blood, bone marrow, tonsil, and adenoids. The object of the present invention can be accomplished by use of cells taken from any of these sources; however, desirable ones are those taken from the tonsil or adenoid.

As the mouse myeloma cell, the use of 8-azaguanine-resistant cell line is favorably suited for the purpose and P3X63Ag8 cell line of BALB/C mouse, P3-NS1/1-Ag4-1 cell line, P3X63Ag 8UI cell line, SP2/0Ag14 cell line, P3X63Ag 8.6.5.3 cell lines, MPC11-45.6 TG 1.7 cell line, and SP-1 cell line are among those publicly known ones.

In the present invention, the human antibody-producing cells are sensitized in the presence of mitogen in vitro prior to the process of fusion of the human antibody-producing cells with the mouse myeloma cells.

In the case of a human being, a normal man has lymphocytes which are capable of producing antibodies against viruses of various types; however, the number of such lymphocytes is so small that they can not be utilized in their original condition for obtaining the desired hybridomas. Also it is true that, when a man is immunized by inoculation with influenza vaccine, antibody-producing cells, which develop an antibody to act against influenza virus, increases in number in his body;

however, the degree of increase is not always enough to give the desired hybridoma efficiently. On the contrary, according to the method provided by the present invention, in which human antibody-producing cells are sensitized in vitro, the differentiation and proliferation of cells are promoted by the sensitization, thus making it possible to increase the number of the desired antibody-producing cells to any desired degree. The intended hybridoma is then obtained efficiently by subjecting the thus sensitized antibody-producing cells to the cell fusion treatment.

No limit is set as to the kind of viruses to be used in the present invention and such viruses as HSV, VZV, CMV, influenza virus, rabies fixed virus, Japanese encephalitis virus, myxovirus, hepatitis B virus, and rotavirus can be used: however, since the antibody-producing hybridoma obtained in the succeeding stage of cell fusion produces an antibody against the virus which is used in the sensitization, the virus to be used for sensitization must be selected in consideration of the usage of the resulting hybridoma. Protein or glycoprotein arising from virus can also be used in the place of virus for carrying out the sensitization.

Though any kind of mitogen can be used so far as it is capable of promoting the differentiation and proliferation of lymph corpuscles, pokeweed mitogen (PWM), protein A, phytohemagglutinin (PHA), and concanavalin A, for instance, may be suggested. Of them all, PWM is most desirable and is usually used in an amount of 1~200 µg/ml, preferably 20~100 µg/ml.

There is no limit placed upon the method and conditions for the sensitization but it is recommendable to have the concentration of the antigen (virus, or protein or glycoprotein arising from virus) kept at 1 ng/ml to 1 µg/ml, the concentration of the lymph corpuscle (antibody-producing cell) at $1\times10^5$ to $1\times10^7$/ml, the culture temperature at 35 to 40° C., and the culture period at 4 to 10 days, preferably at 6 to 8 days. Any culture solution can be used so far as it contains human, bovine, or horse serum, and a culture solution (such as RPMI 1640, for instance) which contains fetal calf serum (FCS) is especially desirable.

The human antibody-producing cell thus sensitized with virus and the mouse myeloma cell are then subjected to the cell fusion according to a known method. To give an example of cell fusion, the antibody-producing cells and the myeloma cells are mixed together at a ratio of 10:1 to 1:100, preferably at a ratio of 1:1 to 1:20. A suitable cell fusion solution, such as RPMI 1640 containing about 35% polyethylene glycol (molecular weight approx. 1,000 to 6,000) and about 7.5% dimethyl sulfoxide is then added thereto and the mixture is stirred for a period of 1 to several minutes at a temperature ranging from room temperature to 37° C. Thereafter, the mixture is diluted slowly with RPMI 1640 containing 10% FCS. The dilution is then adjusted to have a cell density of 1 to $5\times10^5$ cells/ml with a selective liquid culture medium of HAT (hypoxanthineaminopterin-theymidine). This medium is then put into every well of a 96-well plate each 0.2 ml in amount and cultured in the air containing 5% $CO_2$ at 35 to 38° C. for 2 to 3 weeks. In the HAT liquid culture medium, only hybridomas can survive and 8-azaguanine-resistive myeloma cells and fused cells consisting of myelomas themselves can not survive (those antibody-producing cells left unfused perish in the course of a few days). After the culture is over, the antibody titer in the liquid culture medium is checked, and the desired antibody-producing hybridomas only are selectively isolated (cloning). The checking of the antibody titer in the liquid culture medium can be made according to such methods as radioimmunoassay (RIA), enzyme-linked-immunosorbent assay (ELISA) and fluorescent antibody technique which methods aim at the detection of the linkage of antibody to antigen and another type of method in which the activity of an antibody which inhibits the biological activity of a virus. The antivirus-human antibody-producing mouse-human hybridoma selected through the process of cloning in the present invention can be kept in frozen storage and can be mass produced by cultivation according to a proper method.

The cell line of this hybridoma or the cell replicated therefrom also come within the scope of the present invention. Also its variants come within the scope of the present invention so far as they produce substantially the same antivirus-human antibody as the cloned hybridoma.

In this invention, an anti-HSV human monoclonal antibody can be obtained by fusing a human antibody producing cell sensitized to HSV, or a protein or glycoprotein arising from HSV with a mouse myeloma cell in the presence of mitogen in vitro. As HSV, type 1 (for instance, KOS cell line, Hayashida cell line) and type 2 (for instance, YS-4 cell line) are known.

The thus obtained monoclonal antibodies which constitutes a characteristic feature of this invention is an antibody with a molecular weight of about 160,000 of the IgG type having the properties of reacting with the cell membrane and cytoplasm of HSV infected cell of type 1 or type 2 and scarcely reacting with an uninfected cell.

HSV consists of DNA, core protein, capsid, and envelope and an antibody which reacts to the envelope is required in order to inactivate HSV. The envelope is made up of glycoprotein which is known by types B, C, D, E, and F (S.T. Showalter et al., Infection and Immunity, vol. 34, p. 684, (1981)) and the human monoclonal antibody of this invention has a characteristic of reacting mainly with glycoprotein B.

The anti-VZV.human monoclonal antibodies of this invention can be obtained by fusing in vitro a human antibody-producing cell sensitized with VZV or protein or glycoprotein from VZV with a mouse myeloma cell in the presence of mitogen. The characteristic monoclonal antibody thus obtained according to the method provided by this invention reacts with VZV specifically. And especially, human type monoclonal antibody V1 special property of recognizing glycoprotein antigens each having the molecular weight of 108K, 105K, and 62K, and human type monoclonal antibody V2 recognizes glycoprotein antigens each having the molecular weight of 90K and 55K. Both V1 and V2 have an excellent neutralizing activity of inactivating 50% of the viruses in the presence of the complement even at the concentration of monoclonal antibody of 1 µg/ml or less.

The present invention will now be illustrated by the following examples.

EXAMPLE 1

Hybridoma which produces monoclonal antibody against HSV (1) Preparation of HSV antigen Vero cells (about $2\times10^8$ cells) proliferated in a single row were inoculated with HSV (KOS line) of $4.4\times10^6$ PFU (plaque forming units)/ml. After the adsorption was made to proceed for 2 hours at 37° C., the culture was maintained for 24 hours on the MEM medium containing 2% bovine serum. The cells were washed with a phosphate buffered isotonic sodium chloride solution and were then destroyed ultrasonically. After 30-minute centrifugation at 6000 rpm, the obtained supernatant was placed on a 30% sucrose solution in a double layer and treated by centrifugation for 3 hours at a speed of 30000 rpm. The pellet sediment thrown down to the bottom of the centrifuge tube was used as the virus antigen. (2) Sensitization of lymph corpuscle with HSV Human tonsil lymph corpuscles were made to float on the liquid culture medium A (RPMI 1640+20% fetal calf serum +20mM HEPES +2mM glutamine +1mM Na pyruvic acid +0.02 mg/ml serine +80 μg/ml gentamicin). The cell concentration was $17 \times 10^5$ cells/ml. This cell-floated fluid was placed in the 12 wells of a 24-well culture plate, each well containing 1.2 ml. The 12 wells were divided into four 3-well groups and the first group had nothing added, the second group had HSV (antigen) 16 μg protein/ml added thereto, the third group had PWM 20 μg/ml added, and the fourth group had the same amount of HSV and PWM added. The culture plate was incubated in air containing 5% $CO_2$ for 6 days at 37° C. (3) Cell fusion with mouse myeloma cell P3X63Ag 8U1 line (hereinafter abbreviated to P3U1)

P3U1 was incubated in the liquid culture medium B (RPMI 1640 +10% fetal calf serum +2mM glutamine +80 μg/ml gentamicin) beforehand. The cell concentration at the time of use was $6 \times 10^5$ cells/ml. The respective four groups (3 wells of the same group were pooled and mixed) of the sensitized lymph corpuscles of the preceding (2) and P3U1 were washed twice with serum-free RPMI 1640 separately. The lymph corpuscles of the respective groups and $5 \times 10^6$ of P3U1 were placed in separate test tubes. They were centrifuged at a speed of 1500 rpm for 5 minutes and the supernatant was removed. The cell pellets were kept dispersed by tapping the test tubes. 0.5ml of polyethylene glycol (hereinafter abbreviated to PEG) (RPMI 1640 5.75ml +polyethylene glycol 1000 3.5ml +dimethyl sulfoxide 0.75ml) was added thereto to allow the cells to float on the fluid gradually. One minute later 0.5ml of RPMI 1640 was added, again 1 mimute later 1ml of RPMI, again 2 minutes later 4ml of HAT liquid culture medium (RPMI 1640+20% foetal calf serum +80 μg/ml gentamicin +95 μM hypoxanthine +0.4 μM aminopterin +1.6 μM thymidine), and again 2 minutes later 4ml of HAT liquid culture medium were further added. Finally HAT liquid culture medium was added to make 25ml of a cell-floated fluid, which was then placed in a culture plate (of 96 wells) and incubated at 37° C. in the air containing 5% $CO_2$. The half of the liquid culture medium was exchanged with a new HT (obtained by removing A from HAT) liquid culture medium at intervals of one week before hybridoma was obtained.

(4) Measurement of human IgG and anti HSV antibody

The measurements were made according to the enzyme-linked-immunosorbent assay (ELISA). Goat antihuman IgG antibody (10 μg/ml) was fixed to a 96-well plate of Falcon microtest III for measuring human IgG, and 1 μg protein/ml of HSV (KOS line) was fixed likewise for measuring anti HSV antibody respectively. 60 μl of supernatant of hybridoma culture fluid was added to the respective plates and allowed to stand at room temperature for 1 hour. After the plates were washed three times with a phosphate buffered saline (Tween - PBS) containing 0.05% Tween 20, 60 μl of goat antihuman IgG antibody-alkaline phosphatase (diluted 1:2000) was added and was made to undergo reaction at room temperature for 1 hour. The plates were again washed three times with Tween-PBX and 100 μl of a solution prepared by dissolving P-nitrophenyl phosphate in 1M diethanolamine +1mM $MgCl_2$ solution of pH 9.8 at the ratio of 0.6 mg/ml was added thereto. 30 to 60 minutes later, the absorbances at 405 mμ were measured and compared with those of standard IgG solution or standard HSV positive serum to calculate their values.

All the test groups of cells were put into the whole 96 wells of the respective plates and the number of the wells in which hybridomas were found grown, the number of the well in which hybridomas were found producing human IgG, and the number of the well in which hybridomas were found producing anti HSV antibodies were counted and are shown in Table 1. Table 1 shows the cases of lymph corpuscles separated from three different tonsils and all the cases clarify the fact that the highest number of anti HSV antibody producing hybridomas was obtained in the respective cases in which both HSV and PWM were added.

TABLE 1

| Tonsil | Stimulus | whole hybridoma | IgG producing | Anti HSV antibody producing |
|---|---|---|---|---|
| 1 | No stimulus | 21 | 20 | 1 |
|   | HSV | 11 | 9 | 1 |
|   | PWM | 48 | 48 | 4 |
|   | HSV + PWM | 64 | 64 | 58 |
| 2 | No stimulus | 24 | 11 | 0 |
|   | HSV | 28 | 13 | 0 |
|   | PWM | 68 | 68 | 1 |
|   | HSV + PWM | 83 | 80 | 9 |
| 3 | No stimulus | 27 | — | — |
|   | HSV | 36 | 12 | 0 |
|   | PWM | 62 | — | — |
|   | HSV + PWM | 63 | 53 | 1 |

(5) Cloning of anti HSV antibody-producing hybridoma

The cloning was effected according to the limited dilution method. The cells were taken from the wells whose contents were anti HSV antibody positive while confirming the number of the cells and then the cells were laid down in the wells filled with liquid culture medium B at the rate of 1 cell/well or 10 cells/well. When it was noticed that the cells proliferated sufficiently two weeks later, it was inspected for anti HSV antibodies in the supernatant fluids by ELISA test to select anti HSV antibody producing hybridomas.

(6) Preparation of anti HSV monoclonal antibody

D34, one of the thus obtained hybridomas, was cultured in the serum-free ITES culture medium (RPMI 1640, 2 volumes +Dulbecco MEN, 1 volume +F12, 1 volume +insulin 8.5 μg/ml +transferring 2 μg/ml +ethanolamine 20 μM +selenite $2.5 \times 10^{-8}M$). The thus obtained 480ml of the supernatant fluid of the culture medium was ultrafiltrated (with Amicon PM30) to an amount of 14ml. The filtrate was then dialyzed against 0.02M sodium phosphate (pH 7.8) and further put to a column (2cm × 14cm) of DE52 equilirated with a buffer of the same solution. Human monoclonal antibodies were recovered from the fractions (21ml) not adsorbed. The measurement made by the ELISA test method disclosed that the supernatant fluid of the culture medium contained 1.9 µg/ml of human IgG and that the purified preparation of monoclonal antibody contained 28 µg/ml of human IgG. Interpretation made by electrophoresis with the use of dodecyl sodium sulfate-polyacrylamide (5% gel) pointed out the formation of a single band at the site of molecular weight of about 160,000.

EXAMPLE 2

Specificity of anti HSV monoclonal antibody (1) The specificity of the monoclonal antibody was interpreted by the fluorescent antibody technique. Vero cells infected with a KOS line of HSV 1 type were fixed onto slide glasses with acetone and were then allowed to react with a supernatant of the hybridoma culture medium containing monoclonal antibodies for 1 hour at room temperature. After the cells were washed, they were further allowed to react with goat antihuman IgG (diluted 1:10) labeled with fluorescein isothiocyanate at room temperature for 1 hour. The glass slides thus prepared were examined with a fluorescence microscope. The resulting finding was that the monoclonal antibodies which were produced by the hybridomas D34, 7-4, 5-11, H2 and H3.reacted with the cell membrane and cytoplasm of the cells infected with virus and did not react at all with the cells not infected. It was also found that they reacted with the cells infected with the Hayashida cell line of HSV 1 type and the YS-4 cell line of HSV 2 type.

(2) Monoclonal antibody D34, H2, and H3 subclasses and L chain produced from the cloned hybridomas were investigated. The result of the investigation made on the subclasses according to the Ouchterlong's method by use of ovine antihuman IgG1, antihuman IgG2, antihuman IgG3, and antihuman IgG4 showed that all the three monoclonal antibodies presented settling curves with anti IgG1 antibody. It was also made known according to ELISA by use of an alkaline phosphatase-goat antihuman K chain or antihuman λ chain that D34 had a K chain and H2 and H3 ) had λchains.

(3) A study was made according to enzyme-linked-immunosorbent assay (ELISA) to see how D34, H2, and H3 react to herpesviruses. As shown in Table 2, all of D34, H2, and H3 reacted to both HSV type 1 and type 2 viruses but did not react to the uninfeceted host's human enbryonic lung, (HEL) cells. They did not react to other herpes viruses, VZV, CMV, and Epstein-Barr virus (EBV), either. It has accordingly been clarified that the abovementioned three types of monoclonal antibodies react specifcally to HSV type 1 and type 2.

TABLE 2

| Virus | Cell line | ELISA (405 nm) | | |
|---|---|---|---|---|
| | | D34 | H2 | H3 |
| HSV-1 | KOS | 1.1 | 0.8 | 0.5 |
| | FUJINAGA | 1.5 | 1.1 | 0.9 |
| HSV-2 | UW 268 | 1.1 | 0.7 | 0.4 |
| | YS 4 | 1.1 | 0.7 | 0.6 |
| VZV | CAQU | <0.1 | <0.1 | <0.1 |
| | BATSON | <0.1 | <0.1 | <0.1 |
| CMV | AD 169 | <0.1 | <0.1 | <0.1 |
| | HIDAKA | <0.1 | <0.1 | <0.1 |
| EBV | | <0.1 | <0.1 | <0.1 |
| Uninfected HEL | | <0.1 | <0.1 | <0.1 |

TABLE 2-continued

| Virus | Cell line | ELISA (405 nm) | | |
|---|---|---|---|---|
| | | D34 | H2 | H3 |
| Control | | <0.1 | <0.1 | <0.1 |

(4) Immuno precipitation assay of anti HSV monoclonal antibody

Figure 1:
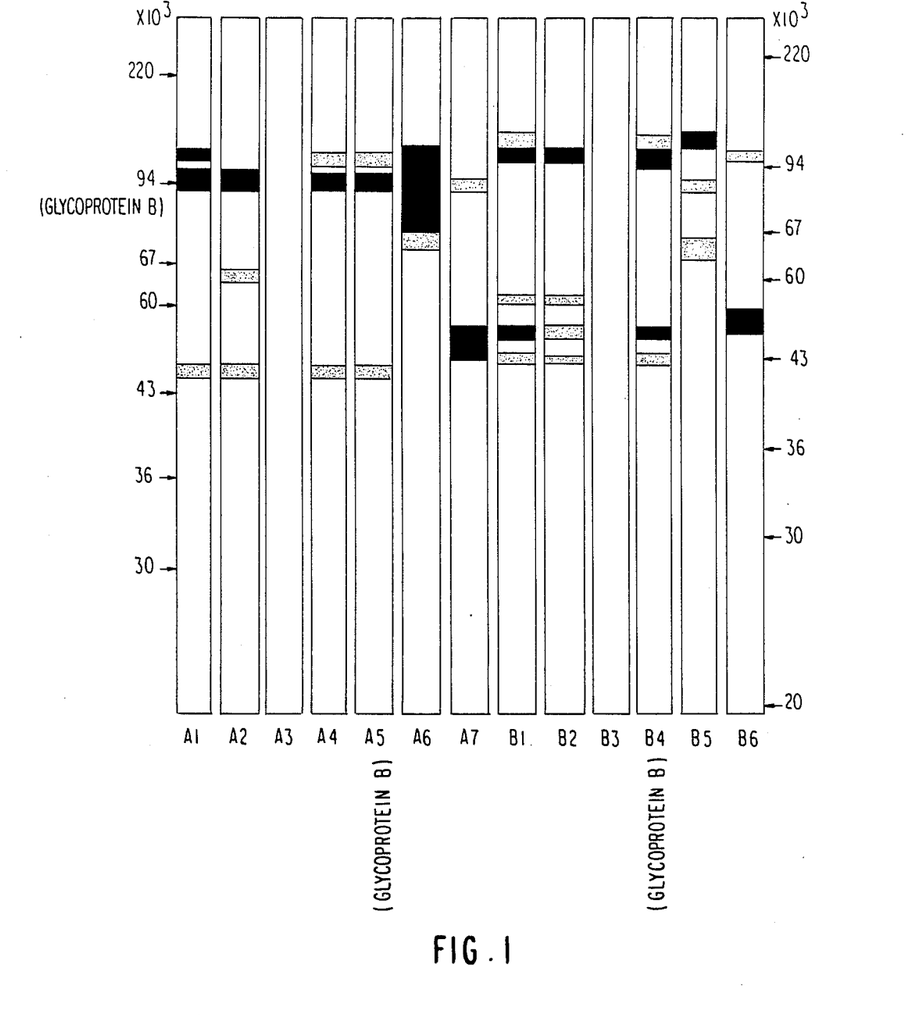
FIG. 1 is an explanatory drawing of X-ray films showing the results of the immuno precipitation analysis of anti-HSV monoclonal antibodies.

An immuno precipitation assay was carried out to determine what component parts make up the microscopic virus body to which human monoclonal antibodies react. Vero cells were infected with HSV type 1 (Fukuda line) or HSV type 2 (UW 268 line) and isotopically labeled with $^3$H-glucosamine or $^{35}$S-methionine. Lysis of the labeled cells was effected with the use of a solution of 0.01M Tris.HCl-0.15M NaCl-1% sodium deoxycholic acid-1% Triton X 100-0.1% sodium dodecyl sulfate (SDS)-1mM phenyl methyl sulfonyl fluoride (pH 7.4). A monoclonal antibody was added thereto to form an antigen-antibody complex, which was then refined through adsorption by use of protein A-cephalose 4B. The refined complex was treated with 0.125M Tris HCl-1% SDS-3% 2-mercaptoethanol-15% glycerin (ph 8.2) for 3 minutes at 100° C. and the resulting supernatant was subjected to electrophoresis on SDS-polyacrylamide gel. After electrophoresis was over, the gel was dried and exposed to X-ray film at −70° C. The results are as shown in FIG. 1 and Table 3, which include the finding that the monoclonal antibodies produced by hybridomas D-34 and 5-11 are both antibodies which react against glycoprotein B of HSV type 1 or type 2 judging from the overlapping patterns of the bands on the X-ray films. A similar experiment showed that 7-4, H-2, and H-3 were also antibodies against glycoprotein B.

TABLE 3

| X-ray film | Virus | Label | Monoclonal antibody |
|---|---|---|---|
| A1 | HSV type 1 | | Human monoclonal antibody D34 |
| A2 | HSV type 2 | | Human monoclonal antibody D34 |
| A3 | None | $^3$H-glucosamine | Human monoclonal antibody D34 |
| A4 | HSV type 1 | | Human monoclonal antibody 5-11 |
| A5 | HSV type 1 | | Mouse anti-glycoprotein B antibody |
| A6 | HSV type 1 | | Mouse anti-glycoprotein C antibody |
| A7 | HSV type 1 | | Mouse anti-glycoprotein D antibody |
| B1 | HSV type 1 | | Human monoclonal antibody D34 |
| B2 | HSV type 2 | | Human monoclonal antibody D34 |
| B3 | None | $^{35}$S-methionine | Human monoclonal antibody D34 |
| B4 | HSV type 1 | | Mouse anti-glycoprotein B antibody |
| B5 | HSV type 1 | | Mouse anti-glycoprotein C antibody |
| B6 | HSV type 1 | | Mouse anti-glycoprotein D antibody |

EXAMPLE 3

Virus neutralizing activity of anti HSV monoclonal antibody

The virus neutralizing activity (potency) of the monoclonal antibody was measured in the following way. 25 μl of a virus fluid (25 μl of a liquid culture medium containing 150 PFU), 25 μl of a monoclonal fluid of graduated dilution, and 25 μl of fresh guinea pig serum (75% W/W) were mixed in a 96-well microplate. After the reaction was continued at 37° C. for 60 minutes, the mixture was transferred to the single row culture of Vero cells in a 96-well microplate to be infected. After the mixture was cultured for two days in the carbon dioxide culture kept at 37° C., the cells were fixed with a 10% formalin solution and dyed with 0.15 crystal violet to observe the plaque formation in each well. The virus neutralizing potency was indicated by the maximum dilution ratio of a monoclonal antibody solution (1 mg/ml) required for decreasing the number of plaques by 80%. As seen from Table 4, monoclonal antibody D34 bonds with HSV but neutralizes neither HSV type 1 nor type 2.

The two other monoclonal antibodies, H2 and H3, neutralized both HSV type 1 and type 2 even in the absence of complement. Table 5 shows the neutralizing spectrum (range) of monoclonal antibody H2. H2 had a high neutralizing potency against all the cell lines in which HSV type 1 and type 2 were used.

TABLE 4

| | Neutralizing potency of monoclonal antibody | | | |
|---|---|---|---|---|
| | HSV-1 (KOS) +C* | −C* | HSV-2 (YS-4) +C | −C |
| D34 | <2 | <2 | <2 | <2 |
| H 2 | 256 | 256 | 192 | 192 |
| H 3 | 192 | 128 | 192 | 128 |
| HIgG+ | 7.7 | 5.1 | 3.8 | 3.8 |

*: Neutralizing potency was determined in the presence of guinea pig complements (+C) or in the absence thereof (−C) (final concentration: 2.5% serum V/V)
+: Normal human beings pooled IgG

TABLE 5

| Neutralization spectrum of monoclonal antibody H2 (range) | | |
|---|---|---|
| | Line of virus | Neutralizing potency |
| HSV type 1 | KOS | 256 |
| | Miyama | 512 |
| | Hagashida 5G | 1024 |
| | Fujinaga 4G | 128 |
| HSV type 2 | UW 268 | 128 |
| | YS-4 (TK−) | 128 |
| | YS-4 (TK+) 4G | 256 |
| | 8204TN 4G | 256 |

EXAMPLE 4

Figure 2:
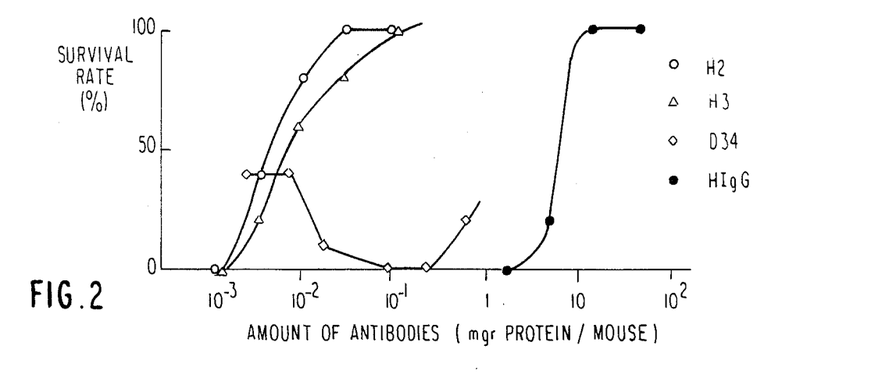
FIG. 2 is a drawing showing the protective effect (survival percentage) of monoclonal antibodies against HSV infection.

Protective effect of various types of monoclonal antibodies against HSV infection Serially diluted antibody solutions (1 ml) were administered abdominally to BALB/c Mice, by giving H2, H3, and H IgG to groups of 5 mice and D34 to groups of 10 mice. 30 minutes later, 2.5 ×10⁵ PFU of HSV type 1 (Miyama GC+line) were abdominally given to the mice and the survival rates were determined 15 days after the infection. The result is shown in FIG. 2. The amount of antibodies required for preventing the infected mice from dying by 50% proved to be more than 0.20 mgr/kgr of H2, 0.35 mgr/kgr of H3, 40 mgr/kgr of D34, and 380 mgr/kgr of H IgG respectively, from which it has been clarified that the preventive effect of H2 is 1900 times as much as H IgG.

EXAMPLE 5

Hybridoma which produces monoclonal antibody against VZV (1) Production of VZV antigen VZV (Kawaguchi cell line) was inoculated into the liquid culture medium of human embryo lung cells (He L) and the cells were taken out with a rubber policeman when cellular degeneration took place. The cells were subjected to the ultrasonic disintegration for 1 minute to destroy them and then centrifuged for 10 minutes at a speed of 3000 rpm. The resulting supernatant was put on a layer of cesium-chloride and was again centrifuged at a speed of 23000 rpm for 3 hours. The VZV were found accumulating in the layer between the concentrations 1.4 and 1.2. This virus fraction was further centrifuged at 25000 rpm for 1 hour and a half to have a sediment, which was then dispersed in phosphate buffered saline and subjected to the ultrasonic treatment three times each for 5 seconds. The virus preparation was inactivated by treating with ultraviolet irradiation and then used for the following experiments.

(2) Sensitization of lymph corpuscle with VZV and production of hybridoma

Human tonsil lymph corpuscles were allowed to float on the liquid culture medium A at the ratio of 2.6×10⁶/ml. VZV (final concentration 17 ng protein/ml) and PWM (20 μg/ml) obtained in the preceding (1) were added thereto respectively and the cultivation was continued for respectively periods of 3, 5, and 7 days. The lymph corpuscles thus sensitized were subjected to cell fusion in the same way as Example 1, (3). The supernatant fluids of the culture medium of hybridomas thus produced were examined by the ELISA test to determine the formation of IgM and IgG anti VZV monoclonal antibodies. The results of examination are shown in Table 6.

It is confirmed from Table 6 that hybridomas which produce monoclonal antibody of IgG type against VZV are produced.

TABLE 6

| Sensitization period (days) | Treatment | The number of wells having hybridoma | The number of wells having IgG anti VZV | The number of wells having IgM anti VZV |
|---|---|---|---|---|
| 0 | — | 91/96 | 0/96 | 0/96 |
| 3 | VZV | 94/96 | 0/96 | 0/96 |
| | VZV + PWM | 93/96 | 0/96 | 0/96 |
| 5 | VZV | 93/96 | 1/96 | 0/96 |
| | VZV + PWM | 95/96 | 2/96 | 0/96 |
| | *VZV | 0/96 | 0/96 | 0/96 |
| | VZV + PWM | 0/96 | 0/96 | 0/96 |
| 7 | VZV | 94/96 | 1/96 | 0/96 |
| | VZV + PWM | 88/96 | 1/96 | 0/96 |

*This is a case in which sensitized lymph corpuscle and P3UI were mixed in the absence of a PEG solution. These groups are presented as a control to confirm that sensitized lymph corpuscle which does not produce hybridoma fails to become IgG anti VZV-positive.

EXAMPLE 6

Lymph corpuscles were separated from the spleen removed by an operative procedure from a patient with disease of autoimmune thrombocytopenia by Ficoll-Paque method. The lymph corpuscles were sensitized by adding VZV (17 μg/ml) and PWM (20 μg/ml) for a period of 6 weeks according to the method of Example 5, (2). The sensitized lymph corpuscles were then subjected to cell fusion according to Example 1, (3). An inspection of the supernatant fluid of the hybridoma culture medium was made using an ELISA test to determine the whole human IgG and IgM, VZV infected Hel cell reactive IgG and IgM, and not infected Hel cell reactive IgG and IgM. The results are shown in Table 7 in terms of the number of wells found positive in the 96-well plate.

It is apparent from Table 7 that monoclonal antibodies of the IgG type selectively reactive to VZV are produced and that the number of hybridomas, which produce monoclonal antibodies selectively reactive to VZV, is remarkably large when sensitized with VZV +PWM. The singular use of PWM produces such hybridomas (6/56) but this method has a demerit in that the number of nonselective hybridomas is large as compared with the case where sensitization is carried out by a sole use of VZV (9/27).

TABLE 7

| Stimulus | Whole hybridoma | Antibody-producing hybridoma | | Anti-VZV-Hel cell | | Anti-Hel cell | |
|---|---|---|---|---|---|---|---|
| | | IgG | IgM | IgG | IgM | IgG | IgM |
| No stimulus | 78/96 | 14 | 14 | 0 | 0 | 0 | 0 |
| VZV | 84/96 | 27 | 17 | 9 | 0 | 0 | 0 |
| PWM | 96/96 | 55 | 42 | 6 | 1 | 0 | 1 |
| VZV + PWM | 96/96 | 69 | 34 | 31 | 1 | 0 | 1 |

EXAMPLE 7

Cloning of anti VZV antibody producing hybridoma and specificity of anti VZV monoclonal antibody (1) Cloning Cells were taken out of the wells which were positive in anti VZV activity and the number of the cells was measured. The cells were put in a 96-well culture plate at a rate of 1 cell/well or 10 cells/well. Seeing the cells proliferating enough 3 to 4 weeks later, the screening was made to see if anti VZV antibody activity developed in the supernatant of the culture medium or not. Necessary cells were mostly selected from those cultured in the well of 1 cell/well as possible. The procedure was repeated 2 to 4 times so that all the clones would come to process anti VZV antibody activity.

Three types of hybridomas were established by mouse-human cell fusion. They were named V1, V2, and V6. V1 has been deposited with the American Type Culture Collection, Rockville, Maryland, and has been given accession number HB 9045.

(2) Specificity of monoclonal antibody

The determination of V1, V2 and V6 subclasses and L chain types was made. Subclasses were determined according to the Ouchterlony's method by use of ovine antihuman IgG 1, antihuman IgG 2, antihuman IgG 3, and antihuman IgG 4. The result of the determination showed that V1, V2, and V6 reacted only with antihuman IgG 1 antibody. Further, the result of the ELISA test made by use of an alkaline phosphatase-goat IgG antihuman K chain or anti λ chain made it clear that all these three monoclonal antibodies had λ chain.

The ELISA test was also conducted by use of various types of viruses or their host cells as antigens to study the immune specificity of V1, V2, and V6. The result is shown in Table 8. V1, V2, and V6 reacted with all the VZV of the experimental 6 cell lines but did not reacted with the host cell HEL at all. Furthermore, it was found that V1 reacted slightly with HSV type 1 and type 2 but V2 and V6 did not react with them. None of the monoclonal antibodies reacted with CMV and EBV either.

| Virus | Cell line | Human monoclonal antibody | | |
|---|---|---|---|---|
| | | V1 | V2 | V6 |
| HSV type 1 | KOS | 0.15 | 0.01 | 0.00 |
| | FUJINAGA | 0.16 | 0.05 | 0.04 |
| HSV type 2 | UW 268 | 0.06 | 0.00 | 0.00 |
| | YS-4 | 0.09 | 0.00 | 0.00 |
| VZV | CAQU | 0.42 | 0.90 | 0.41 |
| | BATSON | 0.39 | 0.33 | 0.35 |
| | KAWAGUCHI | 0.52 | 1.01 | 0.55 |
| | OKA | 1.08 | 1.12 | 1.11 |
| | KOBAYASHI | 0.63 | 0.32 | 0.69 |
| | TUBO | 0.50 | 0.91 | 0.52 |
| CMV | AD 169 | 0.06 | 0.04 | 0.07 |
| | HIDAKA | 0.04 | 0.00 | 0.00 |
| EBV | B95-8 | 0.01 | 0.00 | 0.02 |
| Host cell HEL | | 0.01 | 0.01 | 0.02 |

The numerical values indicate the absorbance (405 nm) obtained by ELISA test.

EXAMPLE 8

Determination of recognition antigen molecule of anti VZV monoclonal antibody

The antigen molecules were determined according to the immuno precipitation method and the dodecyl sodium sulfate-polyacrylamide gel electrophoresis (SDS-PAGE). 1/5 volume of VZV infected cells suspended in trypsin was inoculated in the single row culture (64 cm$^2$) of human embryo lung cells (HEL) on the second day of their incubation. When more than 80% cytopathic effect (CPE) was observed 48 hours after said innoculation started, the culture medium was replaced with 4 ml of 100 μ ci tritium blucosamine hydrochloride salt ([1.6-$^3$H(N)]) glucosamine; 20 ci/mmol; NEN Research Products, Boston, MA)-containing 1/10 glucose MEM-2% FCS or 5 ml of 50 μ ci [$^{35}$S]-methionine (400 ci/mmol; NEN Research Products)-containing 1/10 methionine MEM-2% FCS. The culture was continued at 37° C. for 18 hours and during this time of culture the cells were collected when the CPE extended to the whole cells in the single row. The collected cells were washed with water and then were dispersed and made soluble by subjecting them to the ultrasonic treatment carried out in a RIPA buffer of 10 mM Tris HCl (pH 7.4), 0.15 M Co., St. Loues, Mo.), 1 mM ethylenediaminetetraacetic acid, 1% Triton X-100, 0.1% sodium dodecylsulfate, 1% sodium deoxycholic acid. The thus treated cells were overlaid on a 60% saccharose solution making a volume of 100,000 g, and the mixture was ultracentrifuged for 1 hour to have the insoluble materials removed. The obtained supernatant was taken as the antigen and stored by freezing at −70° C.

150 μl of the hybridoma supernatant and an antigen fraction (200 μl, 400,000 cpm) labeled with [3H]-glucosamine or an antigen fraction (200 μl, 1,200,000 cpm) labeled with [$^{35}$S]-methionine were mixed and its reaction was carried on at room temperature for 30 minutes and further continued at 4° C. overnight. The next morning Protein A-sepharos CL4B beads (3 mg contained in 100 μl of a suspension: Pharmacia Fine Chemicals, Inc., Tokyo) which had been made swollen beforehand was added thereto and the reaction was carried out at 4° C. for 3 hours. The beads which contained the immune complexes were then pelleted by centrifugation and the pellets were washed five times with 2 ml of RIPA buffer and again two times with 2 ml of 10 mM Tris HCl (pH 6.8). 110 μl of SDS-sample buffer was added to the washed immune complexes and was then eluted at 100° C.

The electrophoresis of the specimen solubilized by SDS-PAGE was carried out according to the standard method at room temperature with use of Tris HCl-glycine-SDS buffer (pH 8.3). After having been immersed in an aqueous solution of 1 M sodium salicylate, the slab gel was dried on the filter paper. The dried gel was then examined by exposure on KODAK X-OMATS film at −70° C. for 7 to 21 days.

Figure 3:
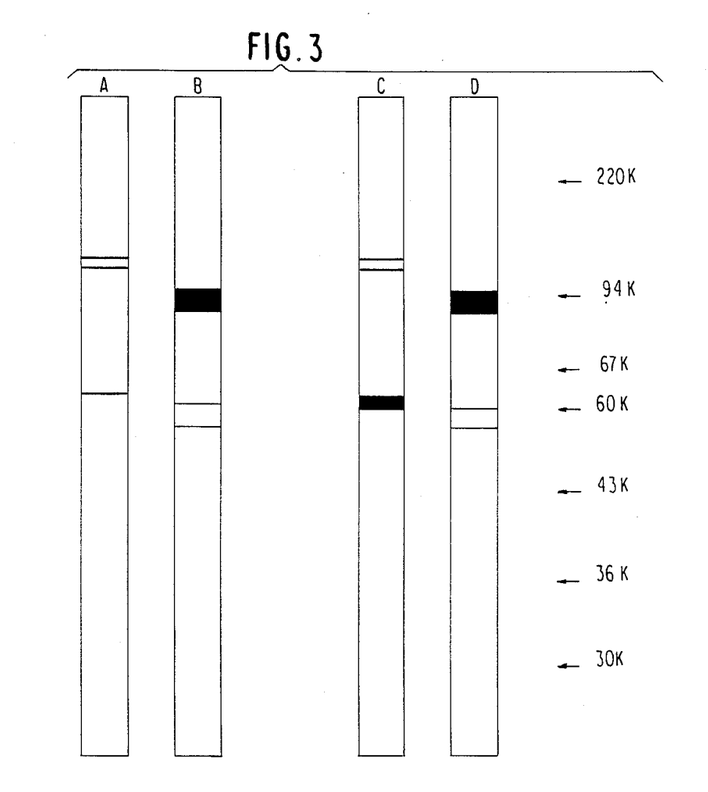
FIG. 3 is SDS-PAGE electrophoretograms showing the anti-VZV monoclonal antibody recognition antigens.

The result is shown in FIG. 3. It has been confirmed that monoclonal antibody V1 recognizes glycoproteins having molecular weight of 108K, 105K, and 62K respectively and monoclonal antibody V2 recognizes glycoproteins having molecular weight of 90K and 55K.

In FIG. 3, the sedimentation of V1 (line A) and V2 (line B) was effected by use of virus antigen labeled with [$^{35}$S]-methionine and the sedimentation of V1 (line C) and V2 (line D) was effected by use of antigen labeled with [$^3$H]-glucosamine. The arrows on the right indicate the migration degrees of protein. K means kilodalton.

Also V6 presented the same electrophoresis pattern as V1.

EXAMPLE 9

Virus neutralizing activity of anti VZV monoclonal antibody

Culture supernatants of anti VZV monoclonal antibody producing cells were collected and the monoclonal antibodies were precipitated by use of 50% saturated ammonium sulfate and the supernatant was dialyzed against phosphate buffered isotonic sodium chloride solution. The obtained dialyzate was subjected to the following experiment as the monoclonal antibody samples. The amount of the monoclonal antibodies contained in the samples was determined by the one-dimensional immunodifusion method with the use of antihuman IgG antibody. The monoclonal antibody sample was diluted by triplicate graduation by using 5% FCS-MEM. The obtained dilution (200 μl), VZV (Kawagushi line, 4000 PFU, 100 μl), and guinea pig complement (1/5 dilution, 100 μl) or 5% FCS-MEM (100 μl) were mixed together and cultured at 37° C. for 1 hour. This solution mixed with viruses was added to the single row culture of HEL prepared beforehand and made the viruses adsorbed at 37° C. for 1 hour. Thereafter, 5% FCS-MEM containing 2.5% methyl cellulose was laid thereon and cultured in the CO$_2$ incubator for 5 to 7 days. Then the infected HEL cells were fixed by use of 10% formalin and were further dyed with 0.15% Crystal Violet to count the number of plaques.

The result is shown in Table 9 indicating the antivirus activity of the monoclonal antibodies V1, V2, and V6 respectively.

It has been made clear that, in the presence of the complement, V1 and V2 require only 1 μg/ml or less for inactivating the viruses by 50%, which means both V1 and V2 have an excellent neutralizing activity.

TABLE 9

| Monoclonal antibody | Monoclonal antibodies required for decreasing plaques by 50% | |
|---|---|---|
| | with no complements | With complements |
| V 1 | 4.0 | 0.84 |
| V 2 | 50 | 0.13 |
| V 6 | 20 | 6.6 |

EXAMPLE 10

Sensitization of CMV antigens in vitro and cell fusion (1) Sensitizing CMV antigen HEL cells were sensitized to 0.1 moi CMV (AD 169 line) and cultured for 7 days in a CO$_2$ incubator. The cells showed undergoing the degeneration up to 100%. The culture supernatant of the cells sensitized to CMV proved to contain CMV of $10^5$ PFU/ml. About 250 ml of the culture supernatant was subjected to centrifugation at 800×g for 10 minutes and further at 10,000×g for 30 minutes and the obtained supernatant was then ultrasentrifuged at 100,000×g for 1 hour. Thus obtained sediment was again suspended in 2 ml of phosphate buffered isotonic sodium chloride solution (pH 7.4) containing 1 mM EDTA and the viruses were inactivated by irradiation with ultraviolet rays. The thus prepared sample was used as the sensitizing antigen.

(2) Sensitization in vitro $1.5 \times 10^6$ of spleen lymph corpuscles obtained from the spleen removed from a patient with idiopathic thrombopenia, about 10 ng protein of CMV antigen, and 20 μg of pokeweed mitogen (PWM) were mixed in 1 ml of liquid culture medium and cultured for 6 days in a CO$_2$ incubator.

(3) Cell fusion

As in the case of HSV and VZV, sensitized lymph corpuscles obtained from 3 ml of the aforementioned dispersion liquid of lymph corpuscles and $5 \times 10^6$ of mouse myeloma cells (P3U1 cell line) were mixed and fused together by means of polyethylene glycol, and then cultured on HAT medium. The result showed that no anti CMV monoclonal antibody producing hybridoma was produced when cell fusion was made without stimulation by CMV antigen, buy many anti CMV monoclonal antibody producing clones were produced from the lymph corpuscles sensitized by antigens. These clones were subjected to the cloning according to the limited dilution method of give seven types of hybridomas, C1, C2, C3, C4.23, C5.3, C6.11, and C7.23. Their immunological specifications are shown in Table 10.

TABLE 10

| Virus | Cell line | Monoclonal antibody | | | | | | |
|---|---|---|---|---|---|---|---|---|
| | | C1 | C2 | C3 | C4.23 | C5.3 | C6.11 | C7.23 |
| HSV type 1 | KOS | 0.0 | 0.0 | 0.0 | 0.0 | 0.0 | 0.0 | 0.0 |
| | FUJINAGA | 0.0 | 0.0 | 0.0 | 0.0 | 0.0 | 0.0 | 0.0 |
| HSV type 2 | UW 268 | 0.0 | 0.0 | 0.0 | 0.0 | 0.0 | 0.0 | 0.0 |
| | YS 4 | 0.0 | 0.0 | 0.0 | 0.0 | 0.0 | 0.0 | 0.0 |
| VZV | CAQU | 0.0 | 0.0 | 0.0 | 0.0 | 0.0 | 0.0 | 0.0 |
| | OKA | 0.0 | 0.0 | 0.0 | 0.0 | 0.0 | 0.0 | 0.0 |

TABLE 10-continued

| Virus | Cell line | Monoclonal antibody | | | | | | |
|---|---|---|---|---|---|---|---|---|
| | | C1 | C2 | C3 | C4.23 | C5.3 | C6.11 | C7.23 |
| CMV | AD 169 | >2.0 | 1.5 | 1.9 | 1.9 | 1.9 | 1.8 | >2.0 |
| | HIDAKA | 1.6 | 0.4 | 1.0 | 1.1 | 1.1 | 1.0 | 1.0 |
| EBV | | 0.0 | 0.0 | 0.0 | 0.0 | 0.1 | 0.0 | 0.0 |
| HEL cells not sensitized | | 0.1 | 0.0 | 0.0 | 0.1 | 0.0 | 0.0 | 0.0 |
| Control | | 0.0 | 0.0 | 0.0 | 0.0 | 0.0 | 0.0 | 0.0 |

The numerical values in the above table indicate the absorbance at 405 nm.

Industrial Application

When the hybridomas of this invention are cultivated in large quantities according to a proper method, anti-virus human antibodies can be obtained from the culture supernatant. Furthermore, it is possible to obtain anti-virus human antibodies from the abdominal dropsy and blood serum of an animal which is made to have tumors arising from the hybridomas transplanted to the animal. The thus obtained anti-virus human antibodies are monoclonal antibodies and can be used for the purpose of making a diagnosis and treatment for various viral infections diseases.

We claim:

1. Mouse-human hybridoma and a cell line arising therefrom both of which produce antivirus-human antibody, obtained by fusing a human antibody producing cell which has been sensitized in vitro with virus of the Herpesvirus family or protein or glycoprotein from said virus in the presence of mitogen with a mouse myeloma cell.

2. Mouse-human hybridoma and a cell line arising therefrom according to claim 1, wherein said antivirus-human antibody is an antibody against herpes simplex virus (HSV) or varicella zoster virus (VZV), or cytomegalo virus (CMV).

3. Mouse-human hybridoma and a cell line arising therefrom according to claim 1, wherein said antivirus-human antibody is an IgG antibody.

4. Mouse-human hybridoma and a cell line arising therefrom according to claim 1, wherein said human antibody producing cell is a cell collected from the spleen, tonsil or adenoid.

5. Mouse-human hybridomas according to claim 1, wherein the hybridoma is hybridoma V1, or V2 and is productive of anti-varicella zoster virus (VZV)-human antibody.

6. Human monoclonal antibody which reacts specifically to varicella zoster virus, wherein the antibody is antibody V2 which recognizes glycoprotein antigens of varicella zoster virus which glycoprotein is gpI having a molecular weight of 90K and 545K.

7. Human monoclonal antibody which reacts specifically to varicella zoster virus, wherein the antibody recognizes glycoprotein antigens of varicella zoster virus which glycoprotein is gpI having a molecular weight of 90K and 55K.

8. A process for preparing mouse-human hybridoma which produces antivirus-human antibody comprising the steps of:

sensitizing a human antibody-producing cell in vitro in the presence of mitogen to virus of the Herpesvirus family or protein or glycoprotein arising from said virus, and fusing said human antibody-producing cell with a mouse myeloma cell.

9. The process for preparing mouse-human hybridoma according to claim 8, wherein said mitrogen is pokeweed mitogen (PWM).

10. The process for preparing mouse-human hybridoma according to claim 8, wherein the sensitization is carried out in liquid culture medium which contains fetal calf serum.

11. The process for preparing mouse-human hybridoma according to claim 8, wherein said virus used for sensitization is a herpes simplex virus (HSV), a varicella zoster virus (VZV), or a cytomegalo virus (CMV).

* * * * *